United States Patent [19]

Benezra et al.

[11] Patent Number: 4,853,338

[45] Date of Patent: Aug. 1, 1989

[54] CYANIDE-FREE HEMOGLOBIN REAGENT

[75] Inventors: Jeffrey Benezra, Bronx, N.Y.; Michael J. Malin, Park Ridge, N.J.

[73] Assignee: Technicon Instruments Corporation, Tarrytown, N.Y.

[21] Appl. No.: 284,804

[22] Filed: Dec. 13, 1988

Related U.S. Application Data

[63] Continuation of Ser. No. 52,646, May 20, 1987, abandoned.

[51] Int. Cl.$^4$ ............................................. G01P 33/48
[52] U.S. Cl. ........................................ 436/66; 356/40; 250/461.2; 436/15; 436/63
[58] Field of Search ............... 436/15, 63, 66; 356/40, 356/355–356; 250/461.2; 435/808; 530/385

[56] References Cited

U.S. PATENT DOCUMENTS 3,874,852 4/1975 Hamill .................................. 436/66
4,185,964 1/1980 Lancaster .............................. 436/66
4,286,963 9/1981 Ledis et al. ........................... 436/63

OTHER PUBLICATIONS

Oshiro et al., *Clin. Biochem.* 15 83 (1982).
Zander et al., *Clin. Chem. Acta.* 136, pp. 83–93 (1984).

*Primary Examiner*—Barry S. Richman
*Assistant Examiner*—Lyle Alfandary Alexander
*Attorney, Agent, or Firm*—Jeffrey M. Greenman

[57] ABSTRACT

A method and reagent useful therein are cyanide-free and capable of providing a rapid indication, e.g., less than 30 seconds, of total hemoglobin in a blood sample, so as to fine particular application in automated hematological instrumentation. The novel reagent comprises an ionic surfactant, a pH of at least about 11.3 and is free of ionic cyanide. The ionic surfactant itself can impart the required pH or a strong base independent of such surfactant may be included.

5 Claims, No Drawings

CYANIDE-FREE HEMOGLOBIN REAGENT

This is a continuation of co-pending application Ser. No. 52,646, filed on May 20, 1987, now abandoned.

BACKGROUND OF THE INVENTION

1. Field of the Invention

The present invention relates generally to the determination of total hemoglobin (Hb) in whole blood or in specifically prepared control and calibrator materials derived from whole blood, and, more particularly, to a method and reagent composition useful for performing such determinations which are free of toxic substances, such as cyanide ions.

2. Brief Description of the Prior Art

The determination of total hemoglobin is indicative of the oxygen-carrying capacity of whole blood. The reference, and most commonly used method, for determination of total hemoglobin is the cyanmethemoglobin method. In this method, ferrous ion (Fe (II)), of heme in hemoglobin, oxyhemoglobin and carboxyhemoglobin of the red blood cell is oxidized to the ferric state (Fe (III)) by ferricyanide to form methemoglobin. Methemoglobin is then combined with ionized cyanide to produce cyanmethemoglobin, which is measured photometrically at 540 nm. For further background, reference is made to Henry et al (Eds.) *Clinical Chemistry*, Harper & Row, Hagerstown, Md. (1974) at page 1131 et seq; Drabkin, *J. Biol. Chem.*, 112:51 (1935); and Van Kampen and Ziljstra, *Advances in Clinical Chemistry*, 8:141–187.

The Hamill U.S. Pat. No. 3,874,852 discloses a reagent for hemoglobin determination, which includes ionic cyanide in an alkaline aqueous solution having a pH of 9. In such reagents, ferricyanide is not present. Rather, the heme is oxidized to the ferric state by atmospheric oxygen. The ferric hemoglobin species then binds to the cyanide ions to produce a chromogen which is measured to quantify the hemoglobin.

Also, the Ledis et al U.S. Pat. No. 4,286,963 discloses a reagent for determining both lymphoid and myeloid leukocytes and hemoglobin in whole blood. The reagent includes a surface active quaternary ammonium salt, a phenyl or phenoxy alkanol, and a polyalcohol in an acidic buffer (pH 3.5–5.0) and does not contain ionic cyanide. The suggestion is made that the lack of ionic cyanide is undesirable and results in instability of the chromogen formed by reaction with the hemoglobin. Ledis et al suggests that, if ionic cyanide is present in the reagent, the reagent should be at an alkaline pH for inclusion of buffered cyanide, so as to obtain a satisfactory hemoglobin derivative.

Oshiro et al, *Clin. Biochem.* 15 83 (1982), teach the use of a reagent for hemoglobin determination which comprises sodium dodecyl sulfate or, equivalently, sodium lauryl sulfate (SLS), an anionic surfactant, and Triton X-100, a nonionic surfactant, in a neutral buffer (pH 7.2). The red blood cells are lysed by the SLS. The presence of Triton X-100 prevents SLS from precipitating at temperatures below 5° C. The reaction is completed within 5–10 minutes and produces a green chromogen having absorption maxima at 539 and 572 nm, the depth of color being indicative of the hemoglobin content.

Zander, Lang and Wolf, *Clin. Chem. Acta*, 136 (1984), also disclose a method for determining total hemoglobin, utilizing a reagent which consists of a nonionic surfactant, such as Triton X-100, dissolved in 0.1N NaOH, a strongly alkaline medium. The reaction is completed within 1–2 minutes and a green chromogen is formed having an absorption maximum at 575 nm and a shoulder at 600 nm. Zander et al specifically state that the method does not function if nonionic surfactants are replaced by either cationic or anionic surfactants.

The high throughput of current automated hematologic systems require the use of methods with rapid turnover, e.g., completion time less than 30 seconds. In the case of hemoglobin determinations, such rapid turnover has only been achieved in the prior art by the use of cyanide-containing reagents of high pH and high cyanide levels. Hence, these reagents are highly toxic and also unstable, since ionic cyanide undergoes base-promoted hydrolysis to form formamide and formate. Consequently, additional cyanide must be introduced in the reagent to compensate for such hydrolytic degradation. Accordingly, there is a need for a method for hemoglobin determinations which has a rapid turnover and does not require the use of cyanide.

The prior art methods described above are characterized by a pH of below 11.3, the use of ionic cyanide, or nonionic surfactants, and completion time to form the chromogen substantially in excess of 30 seconds.

Also, because of environmental reasons, the presence of ionic cyanide in any type of reagent used for analytical purposes is highly undesirable. The disposal of the reaction mixture, or effluent, may require special treatment to reduce the concentration of the ionic cyanide within prescribed limits. Otherwise, if in excess of such limits, disposal of the effluent will require special measures, which are costly. Obviously, effluent disposal is very much simplified if no ionic cyanide, or other toxic material, is present in the effluent.

SUMMARY OF THE INVENTION

In accordance with the invention, a novel assay method and reagent composition are provided which are free of ionic cyanide and capable of performing hemoglobin determinations faster than prior methods, e.g., less than 30 seconds, so as to be particularly suited for present-day automated instrumentation. The assay method and reagent composition of the invention are particularly faster than prior art methods in analyzing blood samples having high levels of carboxyhemoglobin, such as in the blood of patients exposed to high levels of carbon monoxide, and are free of the toxicity associated with the presence of ionic cyanide.

The novel reagent composition of the invention comprises an ionic surfactant, at a pH of at least about 11.3, and is free of ionic cyanide. The ionic surfactant can itself be a base which is effective to impart the required pH. Alternatively, the composition can further include a strong base which is independent of the surfactant.

The novel method of the invention comprises combining the sample with the reagent composition, described above, to form a reaction mixture and then observing the absorbence of the reaction product. The reaction product has a distinct green color and is quite stable. The visible absorption spectrum of the reaction product was found to superimpose with published spectra of heme chloride dissolved in a solvent containing a surfactant, such as hexadecyltrimethylammonium bromide or, equivalently, cetyltrimethyl ammonium bromide (CTAB) at an alkaline pH. It was identified as a ferric protoporphyrin IX derivative in which hydroxide ions are the axial ligands of the centrally coordinated ferric ion (Simplicio and Schwenzer, Biochem. 12 (1973) 1923). The same reaction product, is formed from either native hemoglobin in whole blood, solutions of methemoglobin or hemin chloride.

In the reaction of native hemoglobin in whole blood with the novel reagent composition of the present invention, surfactant rapidly lyses the red blood cells, thereby releasing hemoglobin, and efficiently and completely emulsifying the cellular debris and the high lipid content of lipemic plasma of certain blood samples. Since the reagent completely disperses all sources of turbidity arising from the sample, neither filtration nor centrifugation is required prior to optical measurement.

The hemoglobin is then denatured, with the base and surfactant playing distinct roles. The base provides an alkaline pH which denatures the quaternary structure of the hemoglobin by essentially eliminating electrostatic ("saltbridge" ) interactions. The surfactant denatures the hemoglobin by interacting with the interior hydrophobic portion of the protein to expose the heme. Denaturation caused by base and surfactant, in combination, occurs at a faster rate than achievable by either component alone. The denaturation releases the hemes (each hemoglobin possesses four hemes) from their non-covalent interaction with the hydrophobic interior of globin. The hemes are extracted into the micelles of the surfactant, where contact with atmospheric oxygen causes rapid oxidation of the heme iron to the ferric state (Fe III). Subsequent reaction of the ferric heme with hydroxide ions leads to the reaction product, in which hydroxide ions are axial ligands of the resulting ferric ion. The resulting reaction product is very stable, as evidenced by retention of its absorption spectrum over a period of weeks when the reacted sample is stored at room temperature.

Unlike prior art methods, reliable hemoglobin determinations are made by observing the absorbence of the reaction mixture within about 30 seconds and without the risk accompanying the presence of ionic cyanide.

DESCRIPTION OF THE PREFERRED EMBODIMENTS

The present invention provides a novel method and reagent composition for determining total hemoglobin, which composition comprises an ionic surfactant, has a pH of at least about 11.3 and is free of toxic substances, such as cyanide ion. Sample fluids on which such determinations are performed include fresh whole blood and also specially prepared controls and calibrators derived from whole blood used to calibrate hematology analyzers.

The ionic surfactant of the composition can serve as a base or, alternatively, a strong base independent of the surfactant may be included in the composition to impart the required pH for the reaction. Surfactants suitable to impart the required pH include long-chain alkyltrimethylammonium hydroxides such as octadecyltrimethylammonium hydroxide or, equivalently, stearyltrimethylammonium hydroxide or dodecyltrimethylammonium hydroxide, or equivalently, lauryltrimethylammonium hydroxide or tetradecyltrimethylammonium hydroxide, or, equivalently, myristyltrimethylammonium hydroxide. Surfactants which are suitable in combination with an independent component suitable to impart the required pH include zwitterionic surfactants such as N,N-diethyllaurylamine N-oxide, (DMLAO), N,N-dimethylmyristylamine N-oxide, N,N-dimethylcetylamine N-oxide and N,N-dimethyl-stearylamine N-oxide. Another class of such ionic surfactants are the cationic quaternary ammonium halides, specifically the $C_{12}$–$C_{18}$ alkyltrimethylammonium halides. , For example, the $C_{12}$–$C_{18}$ alkyl can be cetyl or the others noted above. The halide can be chloride or bromide. Further, anionic surfactants may be used, such as an alkali metal salt of the $C_{12}$–$C_{18}$ alkyl sulfates. For example, such surfactants include sodium lauryl sulfate, or, equivalently, lithium dodecyl sulfate or, equivalently, lithium lauryl sulfate and sodium tetradecyl sulfate or, equivalently, sodium myristyl sulfate. In general, the ionic surfactant possesses a hydrocarbon chain of 12–18 carbon atoms, usually unbranched, and one ionic head group. The head group may be cationic, anionic or zwitterionic.

Examples of strong bases which are suitable to impart the required pH include alkali metal hydroxides, such as sodium hydroxide and potassium hydroxide. Another example is a tetralkylammonium hydroxide, where the alkyl group can contain 1–4 carbon atoms, such as tetrabutylammonium hydroxide.

The preferred range of the surfactant concentration is between 2.0–5.0 grams per deciliter. Also, the preferred range of the base concentration, where used independently of the surfactant to establish the required pH, is between 0.4–0.6N.

The method of the present invention generally involves detection of a specific product derived by the reaction of the novel reagent composition of the invention with naturally occurring hemoglobin species present in whole blood sample (or control or calibrator material). Naturally occurring hemoglobin species are deoxyhemoglobin, oxyhemoglobin, methemoglobin, fetalhemoglobin, carboxyhemoglobin and sickle cell hemoglobin. The blood sample is diluted about 250 fold with the reagent composition and the resulting reaction product having a reproducible absorption spectrum with a maximum absorption at 570 nm and a shoulder at 595 nm.

One possible mechanism of the reaction is supported by the following equations:

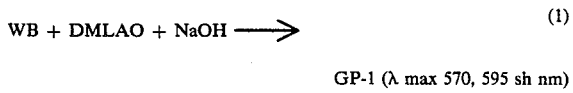

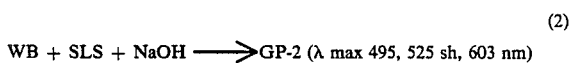

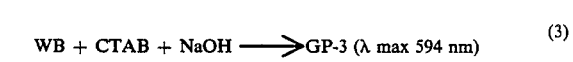

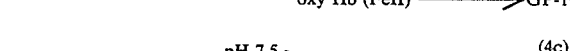

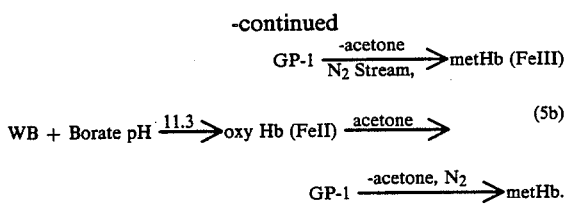

In Equation (1), whole blood (WB) which contains oxyhemoglobin (FeII), combines with 3% N,N-dimethyllaurylamine N-oxide (DMLAO), which is a zwitterionic surfactant, in 0.5N sodium hydroxide (NaOH) to yield a green end-product (GP-1). Product GP-1 has an absorption spectrum having a maximum absorption at 570 nm, and a shoulder at 595 nm. When 3% sodium lauryl sulfate (SLS), an anionic surfactant, in 0.5N NaOH is reacted with whole blood (Equation 2), a product (GP-2) is formed, having an absorption spectrum with maxima at 495 nm and 603 nm and a shoulder at 525 nm. When 3% cetyltrimethylammonium bromide (CTAB), a cationic surfactant, in 0.5N NaOH is reacted with the whole blood (Equation 3), product (GP-3) results, with an absorption spectrum having a maximum at 594 nm.

Equations 1, 2 and 3 illustrate the effects of the surfactant head group charge on the spectrum of the reaction product. The resulting chromogens are now dispersed in surfactant micelles. The spectra of the resulting chromogens, as given above, indicate that the charge of the surfactant head group perturbs the electron configuration of the chromogen and that variations in electrostatic charge of the surfactant head group produce different absorption spectra. In these reactions, the rate of transformation is essentially instantaneous.

The DMLAO/NaOH reagent system (Equation 1) is more completely described by Equations 4a through 5b. In Equation 4a, the blood sample, when diluted with 0.5N NaOH, rapidly yields red-brown alkaline hematin. However, when DMLAO is added to alkaline hematin, GP-1 is formed. However, if blood sample is diluted initially at pH 11.3 by 50 mM borate, instead of 0.5N NaOH, the spectrum of the oxyhemoglobin (having maxima at 540 and 576 nm) was retained. When DMLAO is added to oxyhemoglobin at pH 11.3, GP-1 was formed (Equation 4b). In contrast, when the blood sample was diluted by 50 mM phosphate at (pH 7.5), again oxyhemoglobin spectrum is observed and, after the addition of DMLAO, a yellow-brown product is formed (Equation 4c). Equations 4a and 4b show that the pH of the reaction is important and must be highly alkaline to promote the rapid transformation of oxyhemoglobin to GP-1. When a strong base is used in the absence of surfactant, alkaline hematin is shown to be a precursor to GP-1.

Since alkaline hematin is a ferric heme derivative (Merck Index, 9th Edition), the overall transformation of hemoglobin in blood to produce the absorption spectrum of GP-1 (Equation 1) necessarily involves oxidation of the heme iron ion from the ferrous state (FeII) to the ferric state (Fe III). This conclusion is supported by the reactions indicated in Equations 5a and 5b, where acetone is used in lieu of surfactant. In Equation 5a, when the blood sample was diluted with a reagent comprised of 50% (v/v) acetone and 50% (v/v) of 50 mM borate buffer, (pH 11.3), GP-1 was formed. In Equation 5b, the blood sample was first diluted with borate buffer to give the oxyhemoglobin spectrum, and, after a 1:1 dilution with acetone, GP-1 was again formed. In both Equations 5a and 5b, removal of the acetone by passing a stream of nitrogen through the sample yielded methemoglobin. When acetone is again added to the reaction mixture, as in Equation 5b, GP-1 is regenerated. This substantiates that GP-1, and its characteristic absorption spectrum, results directly from the oxidation of the heme iron ion.

Acetone and DMLAO do not have any common structural features. Hence, their function in the reaction must be to lower the polarity of the reaction medium. Also, other surfactants tested appear to serve a role similar to that of DMLAO. Lowering of the polarity of the reaction mixture serves to release the hydrophobic heme, which is non-covalently complexed with the globin and also is a causal factor for the color (absorption spectrum) of GP-1. In addition, the surfactant causes lysis of the red blood cells and fully disperses the resulting cell ghosts and emulsifies lipids present in the sample, so as to yield a reaction mixture free of turbidity. An advantage of the production of the green end-product, GP-1, is that detection at 570 nm avoids bilirubin interference. Also, GP-1 is generated very rapidly, i.e., within 5 sec after mixing blood and reagent, and is stable for several hours, thus suitable for manual determination of hemoglobin.

Accordingly, a characteristic absorption spectrum given by GP-1 indicative of hemoglobin concentration of the blood sample is achieved using a reagent composition which is completely cyanide-free, which provides distinct advantages in reagent manufacture, transportation, use in the laboratory and waste disposal.

EXAMPLE I

Linearity and Correlation at pH of 13.7

This example illustrates that a linear relationship exists between the total hemoglobin concentration and the resulting absorbence, at a specified wavelength, of the blood sample reacted with the reagent composition of the present invention. Linear behavior, indicative of adherence to Beer's Law, is a desirable property of any colorimetric assay and facilitates standardization and calibration of the assay. Acceptable precision in the field of hemoglobinometry is characterized by a coefficient of variation of ±1.0%.

The reagent composition used in performance of the method was prepared as follows. NaOH (20 g) was dissolved in 800 ml of deionized water. Thereafter, 133.4 ml of 30% aqueous N,N-dimethyllaurylamine N-oxide was added, with gentle mixing. The preparation was brought up to 1 liter with deionized water and filtered to remove particulates (0.2u filter). The resulting solution consisted of 0.5N NaOH and 4% DMLAO and had a pH of 13.7.

Ten tubes of whole blood (10 ml) were collected in standard EDTA Vacutainers (Becton Dickenson Vacutainer Systems, Rutherford, N.J.) and pooled. The cell/plasma ratio of the pooled blood was manipulated to provide a series of samples which varied with respect to total hemoglobin concentration. By "manipulated" is meant to vary in controlled fashion the original hemoglobin concentration, i.e., hematocrit. The tubes of whole blood were centrifuged (5 min.×3000 rpm) to separate the red blood cells from the plasma and buffy coat in each. The buffy coat was discarded and the packed red blood cells were resuspended by volumetric pipetting, in varying proportions, in their native plasma.

Six levels of hemoglobin were generated to cover the clinical range of between 2.5-25 g/dl. Each level was assayed in (5) replicates, by the mixing of 2 ul of the sample with 500 ul of reagent (1:250), prepared as described above. The resulting mixture was then passed through a flow cell (path length=0.80 cm) of a colorimeter equipped with a 570±4 nm band width filter. Absorbence values were taken 25 seconds after mixing sample and reagent. The results are presented in Table I.

TABLE I

| Sample | Hematocrit | $A_{570} \pm CV \%$ |
|---|---|---|
| 1 | 0 | $0.000 \pm 0$ |
| 2 | 15 | $0.083 \pm 0.54$ |
| 3 | 30 | $0.166 \pm 0.29$ |
| 4 | 45 | $0.251 \pm 0.57$ |
| 5 | 60 | $0.333 \pm 0.56$ |
| 6 | 75 | $0.412 \pm 0.29$ |

Table I indicates that the relationship between relative hemoglobin concentrations and measurement at $A_{570}$ is linear with a slope of 1.00 over the clinical range. Also, the calibration curve passes through the origin since absorbence is zero, i.e., $A_{570}=0$ when hemoglobin concentration is zero. Furthermore, the precision of the method, as shown by calculation of the coeffficient of variation is less than or equal to 0.57%, which is well within accepted levels of precision for hemoglobinometry.

EXAMPLE II

Correlation with Reference to Cyanmethemoglobin Method

This example indicates that the results of the present method correlate with those of the cyanmethemoglobin reference method.

Twenty whole blood samples were analyzed for their hemoglobin concentration by the method described in Example I and also by the cyanmethemoglobin reference method using cyanide (CN), described in Van Kampen and Ziljstra, see Table II which was adapted to the TECHNICON H-6000 Flow Cytometry System (Technicon Instruments Corporation, Tarrytown, N.Y.) and operated in accordance with the manufacturer's protocol.

The correlation study yielded the following linear regression equation:

$$(Hb, g/dl)_{CN-Freep} = 0.99 \ (Hb, g/dl)_{REFERENCE} + 0.046 \ g/dl$$

Thus, the method of the invention recovered 99% of the value obtained by the reference method.

TABLE II

| | Correlation of CN-Free Hb Method to the Reference Hb Method | |
|---|---|---|
| Sample | Hb, g/dl, CN-Free | Hb, g/dl, Reference |
| 1 | 11.5 | 11.9 |
| 2 | 12.3 | 12.5 |
| 3 | 14.5 | 14.5 |
| 4 | 8.10 | 8.25 |
| 5 | 11.1 | 11.2 |
| 6 | 11.8 | 11.8 |
| 7 | 16.3 | 16.4 |
| 8 | 8.40 | 8.40 |
| 9 | 16.2 | 16.4 |
| 10 | 10.6 | 10.7 |
| 11 | 11.8 | 11.8 |
| 12 | 11.7 | 12.0 |
| 13 | 9.30 | 9.35 |
| 14 | 8.90 | 8.95 |
| 15 | 14.6 | 14.6 |
| 16 | 11.4 | 11.5 |
| 17 | 7.90 | 7.80 |
| 18 | 8.90 | 8.80 |
| 19 | 10.4 | 10.4 |
| 20 | 14.6 | 14.7 |

In summary, the observed linearity, precision and accuracy of the present method are all well within the acceptable ranges required by clinical hemoglobinometry.

EXAMPLE III

Assay of Blood Poisoned with Carbon Monoxide

The hemoglobin in blood of certain individuals may be "poisoned" so as to contain carboxyhemoglobin due to contact with carbon monoxide. For example, the carboxyhemoglobin in blood samples of heavy smokers and taxi drivers may constitute up to 10% of the total hemoglobin content. An important aspect of any reliable method for hemoglobin analysis is the ability to provide for "poisoned" hemoglobin, the same end product as native hemoglobin, since the spectra of "poisoned" forms of hemoglobin would differ from that of the native hemoglobin.

Two tubes of blood were drawn. One tube was labelled "control". The second tube was labelled "carboxyhemoglobin". The second tube was placed in a hood and a stream of carbon monoxide was bubbled through the contained blood for one hour. The effect of carbon monoxide was observed, the blood acquiring a distinct cherry-red color. The carboxy hemoglobin tube was then found to contain 100% carboxy hemoglobin.

The "control" and "carboxyhemoglobin" tubes were next assayed for hemoglobin by the method of Example I. The reaction products obtained in both tubes were substantially identical, each yielding the characteristic green end product GP-1 with a spectral maximum at 570 nm of substantially the same absorbence, as determined by a rapid scanning spectrophotometer. This supports the mechanism in which the heme is released from the interior of "poisoned" hemoglobin and enters into the reaction, since the same end product is produced, regardless of whether all or a portion of the hemoglobin is "poisoned". Accordingly, the method of the present invention is effective to assay for carboxyhemoglobin, either singly or in the presence of native hemoglobin, as indicated in Table II.

TABLE III

| | Response of "Control" and "Carboxyhemoglobin" Blood | | |
|---|---|---|---|
| Blood | % COHb | $A_{570} \pm CV, \%$ | Hb, g/dl |
| "Control" | 0 | $0.251 \pm 0.57$ | 15.2 |
| "Carboxyhemoglobin" | $100 \pm 2$ | $0.253 \pm 0.58$ | 15.2 |

Both samples were assayed in triplicate to determine % COHb by the method described in N. Tietz, *Fundamentals of Clinical Chemistry*, 1970, p. 836, W. B. Saunders Company.

EXAMPLE IV

Linearity and Correlation at pH of 11.3

This Example illustrates the linearity and correlation of the present method using a cyanide-free reagent composition having a pH of 11.3. In Example I, above, the reagent composition had a pH of 13.7.

One liter of reagent was prepared, which comprised 19.06 g of sodium borate, 66.7 ml of N,N-dimethyl laurylamine N-oxide (DMLAO), (30% stock solution in water), 4.0 g of NaOH and sufficient additional NaOH to adjust the pH to 11.3±0.2. The reagent was filtered (0.2 u) to remove any particulates. The final concentrations of compounds were: 2% DMLAO in 50 mM sodium borate buffer, pH 11.3.

This reagent, and aliquots of the six manipulated blood samples, as obtained in Example 1, were reacted in the manner described in Example I, except that absorbence of the reacted sample was measured 15 sec after mixing. When plotted against hematocrit, the absorbence at 570 nm of the green end-product yields a straight line for hemoglobin concentrations in the range of 2.5-25 g/dl, as shown in Table IV. The correlation study vs the reference method (described in Example II) yielded the following linear regression equation:

$$(\text{Hb, g/dl})_{CN\text{-}Free} = 1.00 \, (\text{Hb, g/dl})_{REFERENCE} + 0.22 \text{ g/dl}$$

TABLE IV

Linearity and Correlation of Cyanide-Free Hb Method at pH 11.3

| Sample | Hct | CN-Free Method | | Reference Method |
|---|---|---|---|---|
| | | $A_{570\,nm}$ | Hb, g/dl | Hb, g/dl |
| 1 | 0 | 0.000 | 0 | 0 |
| 2 | 15 | 0.100 | 5.48 | 5.20 |
| 3 | 30 | 0.201 | 10.8 | 10.4 |
| 4 | 45 | 0.303 | 16.0 | 15.7 |
| 5 | 60 | 0.401 | 21.1 | 20.7 |
| 6 | 75 | 0.503 | 25.9 | 26.0 |

The precision for the CN-free Hb method (5 replicates per Hb level) was 0.57%.

What is claimed is:

1. A method for determining hemoglobin in a blood sample which comprises the step of:
   (a) combining the blood sample with a reagent composition including an ionic surfactant at a concentration of from about 2 to 4 percent weight to volume, which reagent composition has a pH of from about 11.3 to about 13.7 and is free of ionic cyanide to form a reaction mixture;
   (b) measuring the absorbence of said reaction mixture as an indication of hemoglobin in said blood sample.

2. A method of claim 1, wherein (b) comprises measuring the absorbence within 30 seconds of having formed said reaction mixture.

3. The method of claim 1, wherein said ionic surfactant is a zwitterionic surfactant and (b) comprises measuring the absorbence of said reaction mixture at about 570 nm.

4. The method of claim 1, wherein said ionic surfactant is a cationic surfactant and (b) comprises measuring said absorbence at about 594 nm.

5. The method of claim 1, wherein said ionic surfactant is an anionic surfactant and (b) comprises measuring said absorbence at about 603 nm.

* * * * *